(12) United States Patent
Widmer

(10) Patent No.: US 8,049,958 B2
(45) Date of Patent: Nov. 1, 2011

(54) OPTICAL COMPONENT FOR A STEREOMICROSCOPE

(75) Inventor: Hansruedi Widmer, Niederscherli (CH)

(73) Assignee: Haag Streit AG, Koniz (CH)

( * ) Notice: Subject to any disclaimer, the term of this patent is extended or adjusted under 35 U.S.C. 154(b) by 849 days.

(21) Appl. No.: 12/149,094

(22) Filed: Apr. 25, 2008

(65) Prior Publication Data

US 2008/0278800 A1 Nov. 13, 2008

(30) Foreign Application Priority Data

Apr. 27, 2007 (EP) .................................. 07405129

(51) Int. Cl.
*G02B 21/18* (2006.01)
(52) U.S. Cl. .................. 359/373; 359/374; 359/381
(58) Field of Classification Search .......... 359/373–378, 359/381

See application file for complete search history.

(56) References Cited

U.S. PATENT DOCUMENTS

| 5,371,557 | A | 12/1994 | Nanjho et al. |
| 5,956,536 | A | 9/1999 | Dow et al. |
| 2002/0075449 | A1 | 6/2002 | Strahle |
| 2005/0088732 | A1 * | 4/2005 | Spink et al. ............. 359/381 |

FOREIGN PATENT DOCUMENTS

| DE | 3546915 C2 | 10/1985 |
| DE | 10336890 A1 | 3/2005 |
| GB | 2255651 A | 11/1992 |
| JP | 2001-169168 A | 6/2001 |
| WO | WO-2006/000072 A1 | 1/2006 |

* cited by examiner

*Primary Examiner* — Joshua L Pritchett
(74) *Attorney, Agent, or Firm* — Birch, Stewart, Kolasch & Birch, LLP

(57) ABSTRACT

A changing device (60) for an optical examination device, for example a microscope, comprising two beam paths (61.1, 61.2) for a first optical image, and a changing optics (21) which is rotatably arranged in the changing device and is, for example, a Galilei magnification changer having at least two, here three pairs of beam paths (35.1, 35.2 and 45.1, 45.2 and 55.1, 55.2, respectively) which can optionally be switched into the beam paths (61.1, 61.2) of the changing device by rotating the changing optics. In accordance with the invention, the changing optics (21) comprises for each pair of beam paths at least one, here two additional beam paths (36.1, 36.2 and 46.2, 46.2 and 56.1, 56.2, respectively), assigned to the respective pair of beam paths, and the changing device (60) likewise comprises at least one, here likewise two additional beam paths (61.3, 61.4). The changing optics (21) is designed in such a way that it is simultaneously possible during rotation of the changing optics (21) for the beam paths (35.1, 35.2 and 45.1, 45.2 and 55.1, 55.2, respectively) of one pair to be inserted into the beam paths (61.1, 61.2) or removed therefrom, and for the additional beam paths (36.1, 36.2 and 46.2, 46.2 and 56.1, 56.2, respectively) assigned to the respective pair to be inserted into the additional beam paths (61.3, 61.4) of the changing optics or removed therefrom.

13 Claims, 4 Drawing Sheets

OPTICAL COMPONENT FOR A STEREOMICROSCOPE

TECHNICAL FIELD

The invention relates to an optical component having a pair of beam paths and a changing optics which comprises two pairs of beam paths, the changing optics being movably fastened in the optical component in such a way that the two beam paths of one of the pairs of beam paths of the changing optics can optionally be inserted in a beam section of the two beam paths of the optical component.

PRIOR ART

Many different devices are available for optically examining a patient's eye. Some of these comprise a microscope for the stereoscopic viewing of the eye, be this front, rear and/or lateral eye sections. However, there is ever more frequently the requirement that the images of the eye observed by the examiner be viewed simultaneously by a further person, be displayed on a display screen in real time, or else be recorded electronically. To this end, there is inserted into at least one of the two beam paths of the microscope a so-called beam splitter which couples out or deflects a portion of, or the entire radiation from the appropriate beam path to the viewer and guides it, for example, onto an imaging sensor.

WO 2006/000072 (Mitre) describes such an examination device. Inserted into both beam paths of the stereomicroscope in each case is a semitransparent mirror which respectively couples out a portion of the beams and guides it to a camera. The images recorded by the cameras are, finally, displayed on a display screen. There is the problem with this device that the light quantity remaining for the stereoscopic viewing is substantially reduced, since a portion of radiation is coupled out for screen display.

Coupling out the beams for the screen display can, for example, also be performed by deflecting one of the two beam paths completely to a camera, but in this case the stereographic impression disappears completely—both when viewing through the eyepieces and on the screen display.

A further stereomicroscope is described in US 2002/0075449 A1 (Strahle). This comprises two beams for stereoscopic viewing by a first observer, and two additional beams for stereoscopic viewing by a second observer. The two observers can set the imaging magnification by means of corresponding, separate magnifying systems. Although the total light quantity of the respective beam paths is respectively available here for the two viewers, the microscope is expensive and of complicated design, since it has two magnifying devices.

SUMMARY OF THE INVENTION

It is an object of the invention to provide an optical component which belongs to the technical field named at the beginning and enables a simple design and simple handling of an optical examination device equipped therewith.

The way in which the object is achieved is defined by the features of Claim 1. The optical component comprises a pair of beam paths which, in particular, are arranged in such a way that they permit stereoscopic imaging of an object to be imaged. Furthermore, the optical component comprises a changing optics which comprises two pairs of beam paths. The changing optics is movably fastened in the optical component in such a way that one of the two pairs of beam paths of this changing optics can optionally be inserted in a beam section of the two beam paths of the optical component. That is to say, the changing optics optionally enables various images to be implemented with the aid of different imaging properties of the object to be imaged by in each case inserting one of the two pairs of beam paths of the changing optics into the beam path of the optical component. Such a changing optics can be used, for example, to achieve various magnifications of the image. However, it is also possible to vary other imaging properties such as, for example, the size of the illuminated region of the object, the illumination level, the illumination spectrum, the size of the image produced, the brightness of the image, the absorption of specific wavelengths or any other desired properties.

In accordance with the invention, the optical component comprises at least one additional beam path assigned to the two beam paths for the stereoscopic imaging, and the changing optics comprises per pair of beam paths likewise at least one additional beam path assigned to the respective pair and spatially separated therefrom. Furthermore, the changing optics is designed in such a way that, during the optional insertion of the two beam paths of one of the two pairs of beam paths of the changing optics in the two beam paths of the optical component, the additional beam path of the changing optics which is assigned to this pair is simultaneously inserted into a beam section of the additional beam path of the optical component. That is to say, in a first position of the changing optics the first pair of beam paths with the assigned additional beam path is active, and in a second position of the changing optics, the second pair of beam paths with the assigned additional beam path is active.

In this context, the term "assigned" means, inter alia, that the additional beam path can be simultaneously used to observe and illuminate the same region of the object to be imaged, which is also imaged or illuminated with the aid of the beam paths for the first image.

Such an optical component serves for varying the properties of the optical image (also denoted below as first image). They can be used in various devices such as, for example, microscopes or similar devices which can be used for the stereoscopic imaging of an object such as, for example, a patient's eye. The two beam paths of the optical component are typically guided here onto the two eyepieces of such a microscope. The additional beam path serves, for example, for producing an additional image of the object or subject matter to be imaged, for example for viewing by a second viewer, or for displaying the images thus produced on a display screen, or for storing them (electronically). The additional beam path can, however, also be used for illuminating the object to be imaged.

Because of the fact both that the beam paths for the first image and that the additional beam path are combined in a single optical component, the latter can be designed in a fashion that is compact and correspondingly economical in terms of space and cost. Consequently, the complexity of the optical component as such, and that of the optical devices in which such optical components are used, can be reduced and, in addition, the operation of these devices can be simplified, since the properties of the first and the additional image can simultaneously be varied in a fashion tuned to one another by taking the changing optics from the first position into the second (or vice versa).

For example, an additional monoscopic screen display of the object to be imaged can be achieved with the aid of an additional beam path of the optical component (and in accordance with an additional beam path per pair of beam paths of the changing optics). However, depending on the application, it is advantageous when this additional imaging can also be performed stereoscopically. For this case, the optical component comprises not only one additional, but preferably exactly two additional beam paths. The changing optics also correspondingly comprises two additional beam paths per pair of beam paths. During such an embodiment of the invention, however, it is not only that an additional, stereoscopic image is possible with the aid of these two additional beam paths—it is also possible to use these two additional beam paths for various purposes. Thus, for example, one can be used for an additional monoscopic image, and the second can be used for a further, additional monoscopic image. However, one or else both of these additional beam paths could also be used to illuminate the object to be imaged.

Of course, it is also possible to provide three or more additional beam paths in order to produce further monoscopic or stereoscopic images, or to illuminate the object to be imaged (for example with the aid of different illumination sources). However, in order for the space requirement not to become too high and for the optical component not to become too large, this preferably has just two additional beam paths.

In the case of such an optical component with four beam paths (two beam paths for the first image and two additional beam paths), the changing optics likewise has four beam paths per position. These four beam paths per position of the changing optics can in principle be arranged arbitrarily. A simple way of characterizing their mutual position is to use the mutual position of the two planes which are respectively defined by two related beam paths of a pair, or by their beam axes. (It is assumed at this juncture that the two related beam paths of a pair respectively actually define a plane. The case in which this does not happen is not considered here, since this would render the optical imaging impossible, or at least render it very difficult.) The two beam paths of each pair of beam paths of the changing optics define, for example, a first plane, and the two additional beam paths assigned to this pair define a second plane. These two planes can, for example, lie parallel to one another, in which case either they lie at a specific spacing from one another or they are identical, that is to say they define a common plane. The two planes can, however, also enclose an angle such that they intersect in precisely one straight line. The beam paths are preferably arranged in such a way that the two planes intersect in a straight line (denoted below as intersection line) which lies parallel to the optical axis of the optical component.

The beam paths can now be arranged, for example, in such a way that this intersection line lies outside the two first beam paths, and the two planes enclose an angle different from 90 degrees. However, in a preferred way the beam paths are arranged in such a way that the two planes are perpendicular to one another, and the intersection line of the two planes lies between the beam paths for the first image. This arrangement of the beam paths permits the optical component to be designed to save as much space as possible, it also being possible, for example, to optimize the spacing of the two respectively associated beam paths, depending on application.

As mentioned, the optical component is a device with the aid of which it is possible to vary simultaneously the imaging properties of the first and of the additional image. For example, the changing optics can be designed in such a way that the first image and the additional image are made in a first position of the changing optics with a first magnification, and in a second position of the changing optics a different magnification of the first image and the additional image can be achieved. Such an optical component is therefore also denoted below as a changing device. It is to be borne in mind here that in the scope of the present invention the term magnification is also to be understood as a magnification with the factor of one.

In order to change the imaging properties between the respective first and the respective associated additional image, the changing optics preferably comprises for each beam path at least one imaging optics which can optionally be inserted into the relevant beam paths and/or be removed therefrom. In the case of such an embodiment, it is certainly necessary to settle in advance on a few permanently set imaging properties such as, for example, magnification factors, but the corresponding imaging optics can be produced with high quality, for example, with a high luminous level. In order to achieve different magnifications, it would certainly also be possible to use continuously variable imaging optics such as, for example, zoom systems. However, by contrast with the magnification optics with a fixed focal length/magnification, these mostly have a lower luminous level, and the exact magnification factor also cannot always be determined with sufficient accuracy.

Such imaging optics comprise, for example, one lens arrangement each with one or more lenses.

The various imaging optics can, for example, be designed in such a way that they can be inserted individually into a beam path, for example can be pushed radially into the beam path. In order to change the magnification, it would then be necessary to remove an inserted imaging optics and insert a different one. In another exemplary embodiment, a number of imaging optics could, for example, be fastened next to one another on a type of rail, in which case the rail is thus positioned, for example pushed in from the side, until the imaging optics corresponding to the desired magnification is located in the relevant beam path. However, since it must be possible to set the magnification not only for one, but for at least three beam paths, such designs will be quite difficult for the user to handle.

In a preferred embodiment of the invention, the changing optics therefore comprises a carrier device which can be rotated about a rotation axis. Here, all the imaging optics are fastened on this carrier device, being fastened in such a way that the rotation of the carrier device respectively inserts one of the imaging optics into the beam paths. That is to say, depending on position, in this case depending on the angular position of the carrier device, one of the imaging optics provided for a specific beam path is located in the respective beam path.

In order to select the desired position of the imaging optics, that is to say in order to rotate the carrier device, the imaging optics preferably comprises setting means such as, for example, a rotary knob or rotary switch, which can, in particular, be actuated by hand, that is to say is rotatable. The carrier device is advantageously designed in such a way that the imaging properties can be simultaneously set or varied in all the mutually assigned beam paths with the aid of the setting means by rotating the carrier device. However, it is not absolutely necessary for the same imaging properties to result for each beam path given a specific positioning of the carrier device. The imaging optics can, for example, be designed such that for the two beam paths a first magnification factor results for the first image, and for the two additional beam paths a second magnification factor results which is equal to or different from the first magnification factor.

In another exemplary embodiment, the carrier device is designed such that the imaging optics the first beam paths for the first image and the imaging optics for the two additional beam paths can be rotated about the rotation axis independently of one another. In this case, the setting means will also need to be designed such that it is thereby optionally possible for the imaging optics for the two first beam paths, the imaging optics for the two additional beam paths, or else all the imaging optics to be rotated simultaneously about the rotation axis.

Automatic/machine actuation of the setting means is also conceivable in principle, in which case the desired magnification can, for example, be selected with the aid of a computer, and the computer drives a corresponding actuation device such as, for example, a motor connected to the setting means, in such a way that the carrier device is rotated into the appropriate position.

The entire optical component is preferably indicated in a housing. The latter comprises a number of apertures through which the beams from or to the object can enter or exit the housing, respectively. Of course, it would be possible in principle to provide a dedicated entrance and exit aperture, respectively, for each beam path. In order, however, to simplify production, the housing comprises an aperture, arranged on the object side, for the beam paths of the first and the additional image. Furthermore, the housing comprises at least one first aperture, arranged on the observer side, for the beam paths of the first image, as well as at least one second aperture, arranged on the observer side, for the beam paths of the additional image. The two apertures arranged on the observer side are preferably arranged in this case in a fashion spatially separated from one another.

In order to prevent dust particles or the like from soiling the optical systems inside the housing, these apertures are typically sealed with an optically transparent material, for example with appropriately shaped glass sheets, the latter also simultaneously being able to serve as part of the optical systems, for example as objective lens of the associated microscope.

As just described, the two observer-side apertures are typically arranged in a fashion spatially separated from one another. The main reason for this is that the corresponding beam paths are further processed separately from one another as a rule. This separation can be achieved, for example, by simply choosing a sufficiently large spacing between the first two beam paths and the additional beam paths. However, this also thereby has the effect of enlarging the geometrical dimensions of the housing of the optical component, for which reason the latter cannot be designed with the required compactness.

The optical component therefore preferably comprises a deflecting device with the aid of which the beam paths of the additional image are deflected to the second aperture, arranged on the observer side. This deflecting device, which comprises one or more mirrors, for example, is also typically arranged in the housing of the optical component, although this deflection could also be performed outside the housing. That is to say, the beam paths of the additional image run inside the housing substantially in the vicinity of the beam paths of the first image, and are then diverted or deflected by the deflecting device such that they do not exit together with the beam paths of the first image from the first aperture arranged on the observer side, but from the second aperture arranged on the observer side. Of course, the deflecting device could also be designed and arranged to deflect not the beam paths of the additional image, but those of the first image.

As described above, an optical component can, as already mentioned, be inserted into various devices. For example, it can be used in a Greenough stereomicroscope. In the case of such a microscope, the two beam paths for the left and right eye of the observer typically stand in an angle of the order of magnitude of 15°. As a rule, there is no region in which the two beam paths run parallel. In the case of a changing device for such a Greenough microscope, the imaging optics are arranged in such a way that both the two beam paths for the first image and those for the additional image enclose a corresponding angle. Again, the optical components are dimensioned in such a way that the desired image is produced in the observer's eye (or, for example, on an appropriately positioned CCD chip).

Such an optical component is, however, preferably used in a device in which the two beam paths for the first image run parallel in at least one section. This is the case, in particular, for microscopes which use the telescope principle. For such devices, the changing device is advantageously used in that region of the device in which the beams run parallel. Correspondingly, the beam paths of one pair of beam paths of the changing optics also run parallel to one another and parallel to the additional beam paths assigned to this pair.

In a preferred exemplary embodiment of such a changing device, each imaging optics is designed for optically imaging from infinity to infinity, the imaging preferably being direct. Such an imaging optics can be implemented, for example, with a Galilei system. A Galilei system comprises a lens arrangement having a positive lens on one side, and a diverging lens on the other side, the incident beams running parallel and the emanating beams running parallel once again after the magnification (or demagnification). The carrier device therefore comprises a plurality of such Galilei systems each having at least two lenses per beam path, and is therefore also denoted as a lens barrel. In the case of a changing optics having four beam paths per position, one such lens barrel correspondingly also comprises four Galilei systems per position: respectively one for each of the four beam paths (two beam paths for the first image and two for the additional image per position of the changing optics).

This imaging from infinity to infinity enables an arbitrary imaging optics, even no imaging optics (magnification factor one) to be inserted into a beam path. That is to say, in each beam path a Galilei system can be replaced with another Galilei system (simply by rotating the lens barrel), without the need for any further adaptations.

However, instead of Galilei systems it would also be possible to use other imaging optics which enable imaging with the aid of beams that are incident and emanate in parallel. These include, for example, the so-called Kepler imaging systems. However, such systems do not produce an erect image, and so either the user must work with an inverted image, or further means must be provided in order to rotate the image once more.

As already mentioned, such an optical component is preferably used with an optical examination device such as, for example, a stereomicroscope. Such a device typically comprises two beam paths for stereoscopic imaging of an object to be imaged. The optical component can then optionally be connected or joined to the examination device in such a way that the two beam paths of a pair of beam paths of the optical component coincide with a section of the two beam paths of the examination device. Correspondingly, two further beam paths of the examination device from or to the object to be imaged coincide with the beam path or the additional beam paths of the optical component.

Consequently, an optical examination device in accordance with the invention comprises two beam paths for stereoscopically observing an object to be imaged, as well as an optical component or changing device such as has been described above. Such examination devices are frequently used for eye examinations, for example. As already mentioned, a Greenough stereomicroscope or a stereomicroscope using the telescope principle can be involved, for example. As mentioned above, the latter comprise as least one section of beam paths running in parallel. This section is also denoted below as parallel section.

Such an optical examination device with a parallel section typically comprises an objective lens and two eyepieces, that is to say a separate eyepiece for each of the two (at least partially parallel) beam paths, through which the observer can observe the stereoscopic image of the object to be imaged. In the case of such a device, the changing device in the parallel section can now be inserted into the beam paths of the optical examination device between the objective lens and the eyepieces in such a way that the two parallel beam paths for the first optical image of the changing device each form a section of the two beam paths of the optical examination device. That is to say, a light beam which enters the device through the objective lens in the direction of one of the two beam paths of the examination device runs along this beam path, enters the housing of the changing device through the aperture of the latter arranged on the object side, again leaves said housing through the first aperture arranged on the observer side, and then again follows the beam path of the device up to the appropriate eyepiece.

The examination device also correspondingly comprises at least one further beam path which corresponds to the additional beam path of the changing device. That is to say, the at least one additional beam path of the changing device forms, as it were, a section of this at least one further beam path of the examination device.

When these beam paths are used to produce an observable image, the energy flow runs from the object to the observer. However, if one of these beam paths is used to illuminate the object to be imaged, the energy flow runs in the reverse direction from a light source to the object to be imaged and/or illuminated. That is to say, the light emanating from a light source enters the housing of the changing device through one of the apertures arranged on the observer side, traverses the changing optics, leaves the housing through the aperture arranged on the object side, and is guided to the object to be illuminated, for example, to an eye to be examined.

Instead of eyepieces, however, it is also possible in the case of the examination device to provide other optical systems, or to guide the imaging beams onto an imaging sensor, for example. In this case, the object image is observed not through eyepieces but, for example, on a display screen on which the images detected by such an imaging sensor are displayed.

As already mentioned, the beam path or the additional beam paths can, for example, be guided onto appropriate, additional eyepieces for an additional observer. In a preferred embodiment of the invention, the optical examination device comprises an optical imaging device, however, wherein the at least one additional beam path of the changing device can be deflected to this imaging device. The imaging device comprises, for example, an ophthalmoscope, for example a digital ophthalmoscope, in which the region to be imaged is scanned. Thus, for example, it is possible to produce live images of the object to be imaged. Such an ophthalmoscope is also known in English as a scanning digital ophthalmoscope.

If such an ophthalmoscope is used for the eye examination together with an inventive examination device, for example, this enables a user to examine the eye by means of the eyepieces of the device, on the one hand, while at the same time it is possible to display live images of the eye, for example, on a display screen connected to the imaging device, or else to store such images on a suitable storage medium, and this in conjunction with full light efficiency for each of these displays, that is to say without reduced light efficiency owing to the light beams emanating from the eye being split or coupled out.

Since the natural light is frequency insufficient for illuminating the object to be imaged adequately, such examination devices frequency comprise appropriate illuminating means. The provision of illumination is mandatory for some devices such as, for example, a slit lamp microscope. With such devices, this illumination is performed laterally, or from above or below. With other devices, the illuminating beams are also coupled into the observation beam paths, use being made for this purpose of appropriate coupling devices, for example semitransparent mirrors.

In a further preferred embodiment of the invention, at least one of the additional beam paths is used to illuminate the object to be imaged, for which purpose the examination device or the imaging device previously mentioned comprises appropriate illuminating means.

Owing to the fact that one or more of the additional beam paths is/are used to illuminate the object, it is possible, in turn, to avoid the need present in the prior art to insert appropriate mirrors into the observation beam path. That is to say, in this case it is also possible to avoid the need to reduce the light quantity for the stereoscopic observation of the object via the observation beam paths for the additional illumination of the object.

In a preferred embodiment of such an optical examination device, the changing optics comprises per position two additional beam paths such that, for example, one of these can be used for illumination with the aid of an illuminating device of the ophthalmoscope, while the other can be used to produce the live images.

In this case, the illuminating beams run in the changing device in the opposite direction to the observation beams, specifically in a fashion emanating from the illumination source to the object.

Further advantageous embodiments and combinations of features of the invention are to be gathered from the following detailed description and the totality of the patent claims.

BRIEF DESCRIPTION OF THE DRAWINGS

In the drawings used to explain the exemplary embodiment.

Identical parts have been provided with identical reference numerals in the figures as a matter of principle.

Ways of Implementing the Invention

Figure 1:
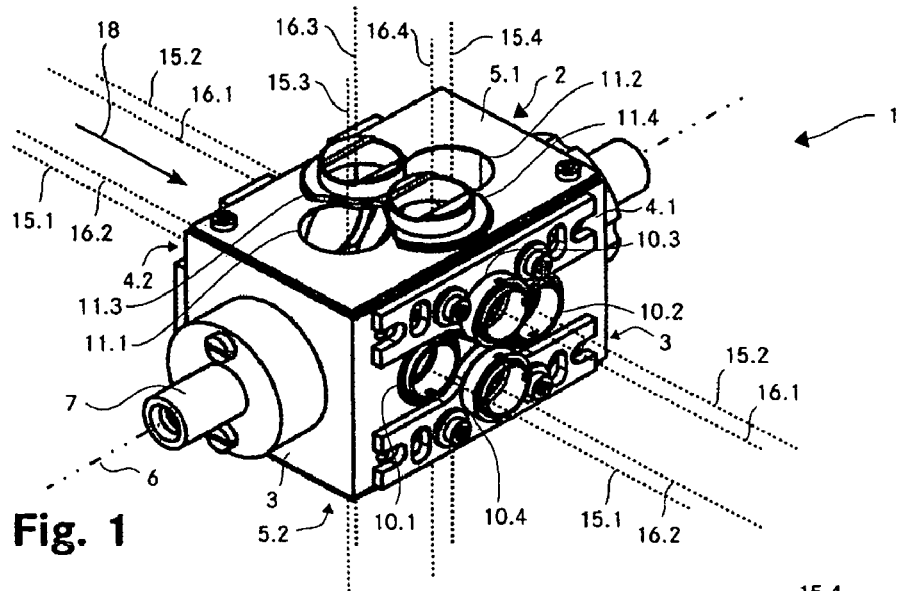
FIG. 1 shows a perspective illustration of a lens barrel for an inventive magnification changer with three magnification stages.

FIG. 1 illustrates in a perspective view a lens barrel 1 for an inventive changing optics, in this case for a magnification changer. The lens barrel 1 comprises a cuboid housing 2 with two essentially square end walls or end faces 3, and two first side walls or side faces 4.1, 4.2 and two second side walls or side faces 5.1, 5.2. In order for it to be possible to rotate the lens barrel 1 about a rotation axis 6, there is flanged on each end face 3 a corresponding axial piece 7 with the aid of which the lens barrel 1 is supported in the magnification changer.

Apertures 10.1, 10.2, 10.3, 10.4 are provided in the side face 4.1, corresponding apertures (only partially visible) likewise being provided in the side face 4.2. The beam paths 15.1, 15.2 and 16.1, 16.2, respectively run through in each case two mutually corresponding apertures in the side faces 4.1 and 4.2 lying opposite one another.

Also provided in the side faces 5.1, 5.2 are apertures 11.1, 11.2, 11.3, 11.4 of such type, which define corresponding beam paths 15.3, 15.4 and 16.3, 16.4, respectively.

The apertures 10.1, 10.2, 10.3, 10.4, and thus also the corresponding beam paths 15.1, 15.2 and 16.1, 16.2 as well as 15.3, 15.4 and 16.3, 16.4, respectively, are arranged here in the form of a cross. That is to say, the beam paths 15.1, 15.2 define a first plane, and the beam paths 16.1, 16.2 define a second plane. These two planes are perpendicular to one another, the intersection line of the two planes lying parallel to the beam paths 15.1, 15.2, 16.1, 16.2, specifically such that it lies between the beam paths 15.1, 15.2, and also between the beam paths 16.1, 16.2. A corresponding statement holds for the beam paths 15.3, 15.4, 16.3, 16.4 in the side faces 5.1 and 5.2.

A lens 12.1, 12.2, 12.3, 12.4 is now respectively mounted from outside or inside in the apertures 10.1, 10.2, 10.3, 10.4 as also in the apertures on the opposite side face 4.2, such that the two lenses which lie in opposite apertures respectively form a magnifying optics, a so-called Galilei system (this has been denoted earlier as imaging optics). However, the term lens is understood not only as a single lens, but can also respectively cover a combination of lenses. Such lenses are fastened in the apertures, typically by means of appropriate lens mounts.

In this way, a respective separate Galilei system lies in each of the beam paths 15.1, 15.2, 16.1, 16.2. In principle, the magnification factors can be selected to be different for each Galilei system by selecting the lenses and their spacings. However, typically at least the magnification factors of the two Galilei systems in the two beam paths 15.1, 15.2 are identical, since these are mostly used for a stereoscopic image of an object to be imaged. Different magnifications would lead in this case to results incapable of being used.

Correspondingly, the magnification factors of the two Galilei systems in the beam paths 16.1, 16.2 are also typically identical. In the example illustrated, the magnification factors of all four Galilei systems are identical in the four beam paths 15.1, 15.2, 16.1, 16.2. It is thereby possible as a result for the image with the aid of the two beam paths 15.1, 15.2, which can, for example, be observed through an eyepiece of an appropriately equipped microscope, to correspond essentially to the additional image with the two beam paths 16.1, 16.2, which is, for example, displayed on a display screen of a computer connected to the microscope.

A magnification changer typically comprises two beam paths for a stereoscopic image as well as two additional beam paths for an additional image or illumination of the object to be imaged. The lens barrel 1 in the first position illustrated in FIG. 1 is now inserted into such a magnification changer in such a way that each of the beam paths 15.1, 15.2 and the beam paths 16.1, 16.2 coincides with in each case one section of the four beam paths of the magnification changer.

By contrast with the apertures 10.1, 10.2, 10.3, 10.4, the apertures 11.1, 11.2, 11.3, 11.4 in the side face 5.1, and the (invisible) apertures in the opposite side face 5.2 are empty, that is to say no lenses are inserted therein. If the lens barrel 1 is now rotated about the rotation axis 6 by 90 degrees into a second position, it is no longer the beam paths 15.1, 15.2, 16.1, 16.2, but the beam paths 15.3, 15.4 and 16.3, 16.4 which coincide with the respective beam paths of the magnification changer. That is to say, the beam paths 15.3, 15.4 and 16.3, 16.4 of the magnification changer no longer run through the apertures 10.1, 10.2, 10.3, 10.4 in the side faces 4.1, 4.2, but through the apertures 11.1, 11.2, 11.3, 11.4 in the side faces 5.1, 5.2. Since there are no lenses in these apertures, the image is not magnified and also not demagnified—the result being, as it were, a magnification factor of one (the total magnification of the microscope typically differing from one, since the microscope comprises further optical components which influence the magnification).

As illustrated in FIG. 1, it is possible in this way to implement three different magnifications with the aid of one lens barrel 1. Assuming that the object to be observed is located in the illustration in accordance with FIG. 1 on the left downstream of the lens barrel 1, the light beams emanating from the object run in the direction of the arrow 18 up to the lens barrel 1, enter the side face 4.2 through the apertures therein, traverse the appropriate Galilei systems and exit from the lens barrel 1 again through the apertures 10.1, 10.2, 10.3, 10.4, a first magnification being implemented by the Galilei systems. How high the corresponding magnification factor is depends both on the lenses used and on their spacing, and can in principle be freely selected. If the lens barrel 1 is now rotated by 90 degrees in a clockwise or an anticlockwise sense, the light beams run through the apertures 11.1, 11.2, 11.3, 11.4 in the side face 5.1, as well as the apertures in the side face 5.2. Since there are no lenses located in these apertures, the image is not magnified or demagnified—the result being, as it were, a second magnification factor of one. If the lens barrel 1 is rotated further by 90 degrees, the light beams emanating from the object run in turn through the apertures in the side faces 4.1 and 4.2, but this time in the opposite direction, that is to say they enter the lens barrel 1 through the apertures 10.1, 10.2, 10.3, 10.4 in the side face 4.1, traverse the corresponding Galilei systems in the reverse direction and exit from the lens barrel 1 again through the apertures in the side face 4.2. In this way, the Galilei systems implement a third magnification which, in turn, depends on the lenses used and their spacing.

Figure 2:
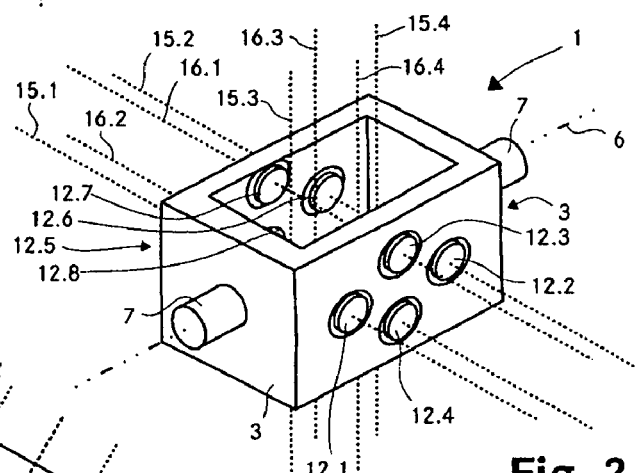
FIG. 2 shows a diagrammatic illustration of a further lens barrel for three magnification stages.

FIG. 2 shows for the sake of a better overview a diagrammatic illustration of the lens barrel 1 from FIG. 1. Identical parts are provided here with identical reference numerals.

Since, in any case, no lenses are inserted into the apertures 11.1, 11.2, 11.3, 11.4 of the side faces 5.1, 5.2, these side faces 5.1, 5.2 have been left out in the diagrammatic illustration in FIG. 2 by contrast with the illustration in FIG. 1.

Figure 3:
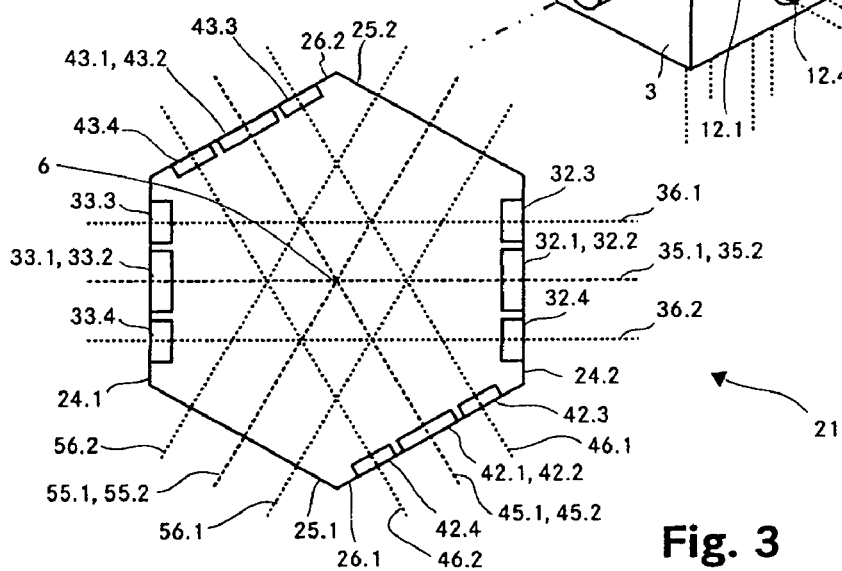
FIG. 3 shows a diagrammatic illustration of a further lens barrel for five magnification stages.

FIG. 3, shows, in turn, a diagrammatic illustration of a further lens barrel 21 for five magnification stages. Here, the lens barrel 21 is shown from the view in the direction of the rotation axis 6 which is, consequently, to be recognized as a point in the middle, that is to say in the manner of a sectional illustration.

The basic shape of this lens barrel 21 is not square, as in the case of the lens barrel 1 from FIG. 1, but hexagonal. The lens barrel 21 is therefore designed as a regular hexagonal prism with three pairs of mutually opposite side faces 24.1, 24.2, 25.1, 25.2, 26.1, 26.2.

Located once again in the side faces 24.1, 24.2 are apertures into which lenses 32.1, 32.2, 32.3, 32.4 and 33.1, 33.2, 33.3, 33.4, respectively, are inserted. Here, as well, two lenses, specifically the lenses 32.1 and 33.1, 32.22 and 33.2, 32.3 and 33.3 as well as 32.4 and 33.4 each respectively form a Galilei system and define, as it were, the beam paths 35.1, 35.2, 36.1 and 36.2.

Similarly, apertures into which lenses 42.1, 42.2, 42.3, 42.4 and 43.1, 43.2, 43.3, 43.4, respectively, are inserted are located in the side faces 26.1, 26.2. Here, as well, the lenses 42.1 and 43.1, 42.22 and 43.2, 42.3 and 43.3 as well as 42.4 and 43.4 respectively form a Galilei system and thus define the beam paths 45.1, 45.2, 46.1 and 46.2.

In order to demonstrate that the magnification of the Galilei systems of the side faces 24.1, 24.2 and 26.1, 26.2, respectively, are different, the lenses 32.1, 32.2, 32.3, 32.4 and 33.1, 33.2, 33.3, 33.4, respectively, are illustrated more thickly than the lenses 42.1, 42.2, 42.3, 42.4 and 43.1, 43.2, 43.3, 43.4, respectively.

Finally, here as well no lenses are inserted into the apertures in the side faces 25.1, 25.2, and so the light beams can pass unhindered from the object through the lens barrel 21 along the beam paths 55.1, 55.2, 56.1 and 56.2.

Running through respectively two mutually opposite side faces 24.1, 24.2 and 25.1, 25.2 and 26.1, 2.6, respectively, are the corresponding pairs of beam paths 35.1, 35.2 and 45.1, 45.2 and 55.1, 55.2, respectively, as well as the respective associated additional beam paths 36.1, 36.2 and 46.1, 46.2 and 56.1, 56.2, respectively.

Consequently, five different magnifications can be implemented with the aid of this lens barrel 21: specifically, two different magnifications with the aid of the Galilei systems in the side faces 24.1, 24.2, that is to say one in each direction. There are two further magnifications with the aid of the Galilei systems in the side faces 26.1, 26.2, as well as the magnification with the factor 1 when the lens barrel 21 is rotated such that the beam paths 55.1, 55.2, 56.1 and 56.2 through the side faces 25.1, 25.2 are located in the beam path from the object to the observer.

Figure 4:
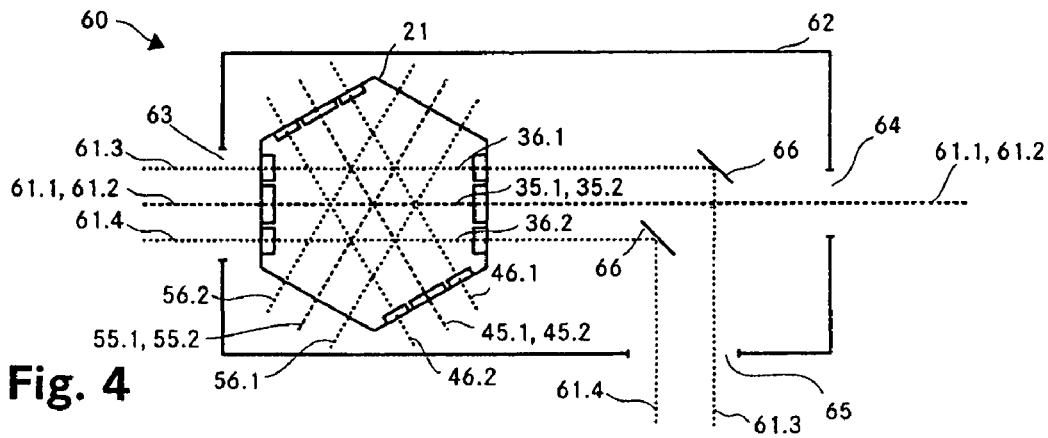
FIG. 4 shows a diagrammatic illustration of a magnification changer with the lens barrel from FIG. 3.

A magnification changer 60 in accordance with the invention is illustrated in FIG. 4 schematically in a housing 62 which encompasses a lens barrel 21 in accordance with FIG. 3. Also illustrated are four beam paths 61.1, 61.2, 61.3 and 61.4. The beam paths 61.1, 61.2 serve the purpose of stereoscopic imaging, and the beam paths 61.3 and 61.4 are the additional beam paths assigned to the two beam paths 61.1, 61. The housing 62 comprises an aperture arranged on the object side, denoted below as entrance aperture 63, and a first aperture arranged on the observer side, denoted below as exit aperture 64, and a second aperture arranged on the observer side, denoted below as exit aperture 65. (Although light beams can pass through these apertures in both directions for the purpose of illumination or observation, these apertures are denoted as entrance and exit apertures, respectively.) The entrance aperture 63 here an individual large aperture such that all the beam paths 61.1, 61.2, 61.3 and 61.4 can enter the housing 62 of the magnification changer 60 through this common aperture. In the example illustrated, there is inserted directly into this entrance aperture 63 a lens which serves as front lens of the associated optical examination device. However, the entrance aperture 63 can also have a number of small apertures such that a separate aperture is respectively present for each beam path 61.1, 61.2, 61.3, 61.4. Of course, these two options can also be mixed such that a number of apertures are present for one or more beam paths, respectively.

Of course, a corresponding statement also holds for the exit apertures 64, 65, the beam paths 61.1, 61.2 running through the first exit aperture 64, and the beam paths 61.3, 61.4 running through the second exit aperture 65.

In the illustrated example in FIG. 4, the light beams from the object to be imaged all enter the magnification changer 60 in a parallel fashion through the entrance aperture 63, that is to say the front or objective lens, traverse the lens barrel 21 and exit again from the lens barrel 21 in a parallel fashion. The light beams emanating from the object, which traverse the lens barrel 21 along the beam paths 61.1, 61.2, exit in parallel again from the magnification changer 60 through the first exit aperture 64. By contrast therewith, the light beams emanating from the object, which traverse the lens barrel 21 along the beam paths 61.3, 61.4, exit from the magnification changer 60 through the second exit aperture 65. To this end, said magnification changer 60 comprises two mirrors 66, one of the mirrors 66 each being positioned in each of the beam paths 61.3, 61.4. Since the beam paths 61.3, 61.4 are substantially located one above another, the mirrors 66 are arranged offset one behind another in the direction of the beam paths, so that the deflected light beams do not coincide. The mirrors 66 are arranged here such that the light beams are deflected at right angles, that is to say the mirrors are arranged at an angle of 45 degrees with reference to the beam paths 61.3, 61.4. However, it would also be possible to arrange the mirrors 66 at another angle, or to use other deflecting means such as, for example, prisms, in order to deflect the beam paths 36.1, 36.2 to an arbitrarily positioned second exit aperture 65. However, it is also advantageous in these cases when the beam paths 61.3, 61.4 also run parallel after being deflected, such that they can be used for an additional, stereoscopic image of the object to be imaged.

It would also be possible for the mirrors 66 to be used to deflect the beam paths 61.1, 61.2 to the second exit aperture 65, in which case the beam paths 61.3, 61.4 would again run in parallel and exit from the housing 62 of the magnification changer 60 through the first exit aperture 64.

In order to prevent beam transitions of the light beams emanating from the object between the various beam paths 61.1, 61.2, 61.3, 61.4, it is also possible to provide suitable diaphragms (not illustrated). These can be arranged at any desired location along these beam paths 61.1, 61.2, 61.3, 61.4, that is to say both outside and inside the magnification changer 60, and also outside or inside the lens barrel 21.

Figure 5:
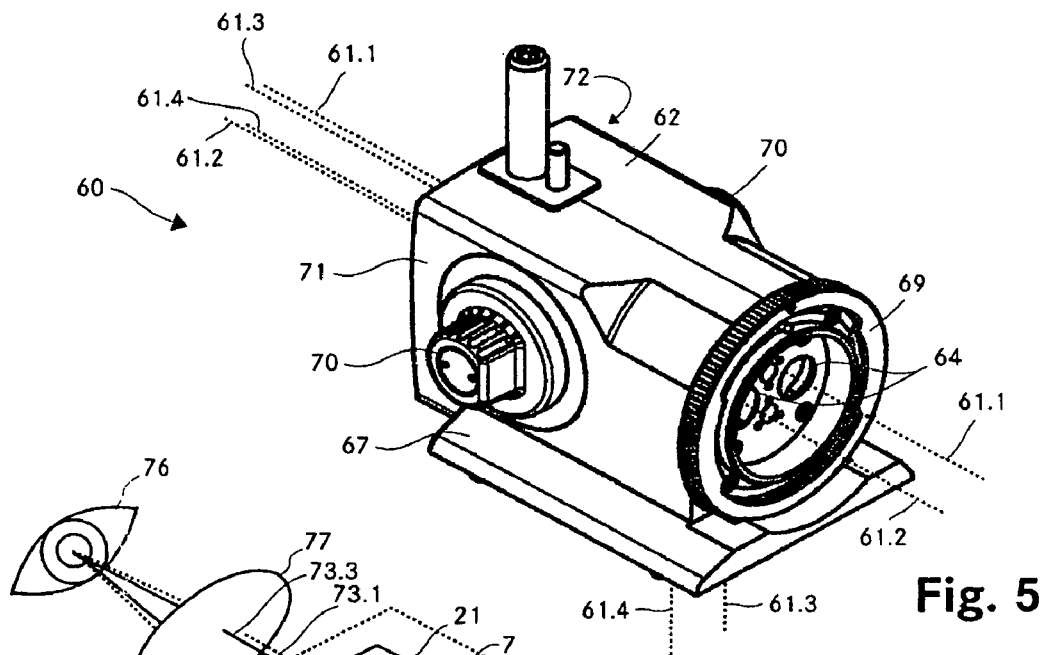
FIG. 5 shows a perspective illustration of an inventive magnification changer.

FIG. 5 shows, in turn, the magnification changer 60 from FIG. 4, here in a detailed, perspective illustration with the incident and emerging beam paths 61.1, 61.2, 61.3, 61.4. The housing 62 comprises a base 67 with the aid of which the magnification changer 60 can, for example, be fastened on a stand, this base 67 also comprising an aperture (not visible) through which the light beams exiting the second exit aperture 65 can pass unhindered through the base 67 along the beam paths 61.3, 61.4.

The housing 62 is essentially of cuboid design, that end with the exit aperture 64, which can be seen here as two separate exit apertures 64 for the beam paths 61.1, 61.2, comprising a bayonet lock 69. This bayonet lock 69 can be used to interconnect the magnification changer 60 and the downstream optical unit, for instance an appropriate observation tube such as, for example, a binocular tube. The housing 62 can also comprise such a bayonet lock at that end with the entrance aperture 63 (not visible in FIG. 5), in order to connect the magnification changer 60 to a preceding optical unit, for example an objective. That is to say, these bayonet locks can be used for optionally inserting the magnification changer into an optical examination device, this being done, in particular, in a section in which the light beams from the object run parallel to one another.

The housing 62 comprises at its front side face 71 a rotary switch 70 with the aid of which the lens barrel 21 located in the interior of the housing 62 can be rotated about its rotation axis 6 in order to set the desired magnification stage. For this purpose, the lens barrel 21 is, for example, supported with its axial pieces 7 in corresponding apertures in the housing 62. In order for the operator to be able to set the desired magnification optionally with the left or right hand, a corresponding rotary switch 70 is provided on the side face 72 opposite the side face 71.

Figure 6:
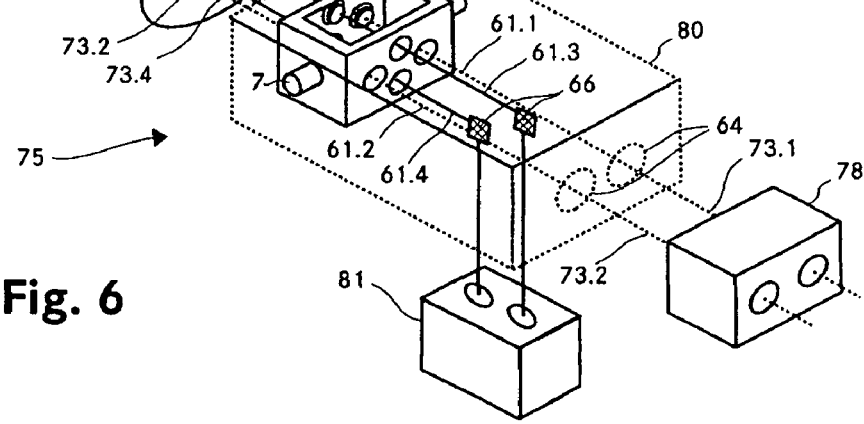
FIG. 6 shows a diagrammatic illustration of the beam path of an inventive examination device.

FIG. 6 shows diagrammatically the beam path in an inventive examination device, in this case in a stereomicroscope 75 for examining an eye 76 with the aid of two stereoscopic beam paths 73.1 and 73.2. The magnification changer 80 used here (illustrated by dashes) comprises a lens barrel 21 as illustrated in FIG. 2. Also illustrated is the objective lens 77 of the stereomicroscope 75 which, as described further above, is inserted into the entrance aperture of the changing device. This objective lens 77 varies the course of the light beams emanating from a specific point of the eye 76 in such a way that these run parallel downstream of the objective lens 77 (seen from the eye 76). These parallel light beams traverse the stereomicroscope 75 along the beam paths 73.1, 73.2, 73.3, 73.4. They correspondingly traverse the magnification changer 80 along the beam paths 61.1 and 61.2 or 61.3 and 61.4, the corresponding images (or illuminations) being performed in accordance with the current position of the lens barrel 21. The light beams leave the lens barrel 21 in parallel, in turn, the light beams running along the beam paths 73.3, 73.4 and 61.3, 61.4, respectively, being deflected downwards by the two mirrors 66 such that they exit through corresponding apertures on the underside of the magnification changer 80 (or enter from below through the apertures and are deflected by the two mirrors 66 in the direction of the eye 76). The light beams running along the beam paths 73.1, 73.2 and 61.1, 61.2, respectively, exit from the exit apertures 64 and are guided to the binocular tube 78 of the stereomicroscope 75. The binocular tube 78 comprises per beam path 73.1, 73.2 and 61.1, 61.2, respectively, one positive lens (not illustrated) each which produces from the parallel light beams in the focal plane of this positive lens an image which can be observed through the eyepieces (not illustrated).

The light beams running along the beam paths 61.3, 61.4 and deflected by the mirrors 66 are guided to a digital ophthalmoscope 81 outside the magnification changer 80.

Like the magnification changer 60 from FIG. 5, the magnification changer 80 also comprises at least one rotary switch 70 which cooperates with the axial pieces 7 in such a way that the lens barrel 21 can be rotated by rotating the rotary switch about the rotation axis 6 of the lens barrel 21. By rotating the lens barrel 21 about its rotation axis 6, it is respectfully possible for a Galilei system to be inserted into each of the beam paths 73.1, 73.2, 73.3, 73.4 and 61.1, 61.2, 61.3, 61.4, respectively, or to be removed from the relevant beam path. That is to say, the magnifications in all the beam paths 73.1, 73.2, 73.3, 73.4 and 61.1, 61.2, 61.3, 61.4, respectively, are switched over simultaneously by rotating the lens barrel 21.

Figure 7:
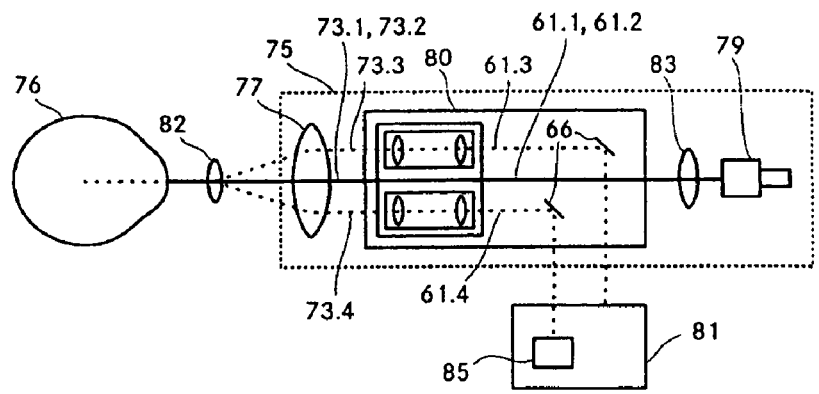
FIG. 7 shows a diagrammatic illustration of an inventive examination device with a digital ophthalmoscope connected to the magnification changer.

FIG. 7 shows, in turn, the stereomicroscope 75 for examining the eye 76 with the digital ophthalmoscope 81 connected thereto, this time in another diagrammatic illustration. In addition to the objective lens 77, this illustration depicts an auxiliary lens 82 which, for example, enables the fundus of the eye 76 to be imaged. Also illustrated here are the positive lenses 83 for producing the stereoscopic image which can be viewed by means of the eyepieces 79.

The digital ophthalmoscope 81 has a light source 85 whose light is guided to the eye 76 via the beam path 61.4 or 73.4, and is used to illuminate the eye 76. The light beams reflected by the eye 76 pass (inter alia), via the beam paths 73.1, 73.2 and 61.1, 61.2, respectively, and the positive lens 83, to the eyepieces 79. However, the light beams reflected by the eye 76 also pass again via the beam path 73.3 or 61.3 to the digital ophthalmoscope 81 which, for example, produces live images of the eye 76 therefrom and displays then, for example, on a computer monitor.

Figure 8:
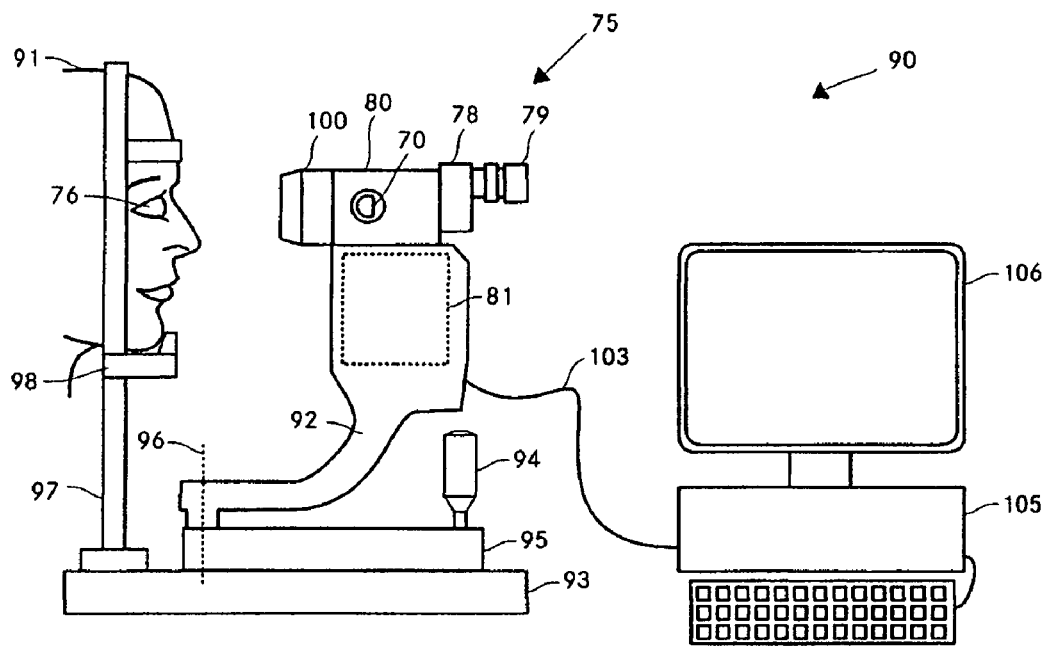
FIG. 8 shows a further diagrammatic illustration of the examination device from FIG. 7.

This is to be seen, for example, in FIG. 8, which shows diagrammatically a possible implementation of a stereomicroscope 75 to which a digital ophthalmoscope 81 is connected. FIG. 8 shows an examination device 90 for examining the eye 76 of a patient 91. The examination device 90 comprises a stereomicroscope 75, which is seated on an L-shaped holding arm 92 which is fastened on a table 93. The holding arm 92 is connected in a fashion rotatable about the axis 96 to a cross slide 95 which can be moved in all three spatial directions with the aid of the lever 94 and be positioned precisely at a desired position on the table 93. Also fastened on the table 93 is a holder 97 with a chin support 98, the head of the patient 91 being positioned in the holder 97 such that the chin of the patient 91 is supported on the chin support 98.

The eye 76 of the patient 91, or a section thereof, can now be observed and examined with the aid of the stereomicroscope 75. The stereomicroscope 75 comprises an objective 100 with the objective lens 77 (not visible), a magnification changer 80 with a rotary switch 70, as illustrated in FIGS. 4 and 5, for example, a binocular tube 78 and two eyepieces 79.

In the example illustrated, the digital ophthalmoscope 81 is integrated directly into the upper part of the holding arm 92 such that when being mounted on the holding arm 92 the stereomicroscope 75 is simultaneously also connected to the digital ophthalmoscope 81.

The digital ophthalmoscope 81 is, furthermore, connected via a cable 103 to a computer 105 on whose display screen 106 it is possible to display images recorded by the digital ophthalmoscope 81, for example.

A further example of a lens barrel 101 for an inventive changing optics is illustrated in FIGS. 9 to 12. In this case, as well, the lens barrel 101 serves the purpose of changing the magnification of the image, not, however, for a microscope using the telescope principle, but for a Greenough microscope. In the illustrations of FIGS. 9 to 12, the object to be imaged is respectively located to the left of the lens barrel 101. In one of its side faces, the lens barrel 101 comprises three imaging optics 112.1, 112.2, 112.3, which are inserted into corresponding apertures and through which beam paths 115.1, 115.2 and 116.1 run or are defined. Furthermore, in others of its side faces the lens barrel 101 comprises three further imaging optics 111.1, 111.2, 111.3 through which beam paths 115.3, 115.4 and 116.3 run or are defined.

The beam paths 115.1, 115.2 form a first pair of beam paths for a stereoscopic, first image of the object with a specific magnification, and the beam path 116.1 is an additional beam path, assigned to the beam paths 115.1, 115.2, for additionally imaging or illuminating the object with corresponding imaging properties. The beam paths 115.3, 115.4 form a second pair of beam paths for a stereoscopic, first image of the object with a magnification other than the imaging along the beam paths 115.1, 115.2, and the beam path 116.3 is an additional beam path, assigned to the beam paths 115.3, 115.4, for additionally imaging or illuminating the object.

Figure 9:
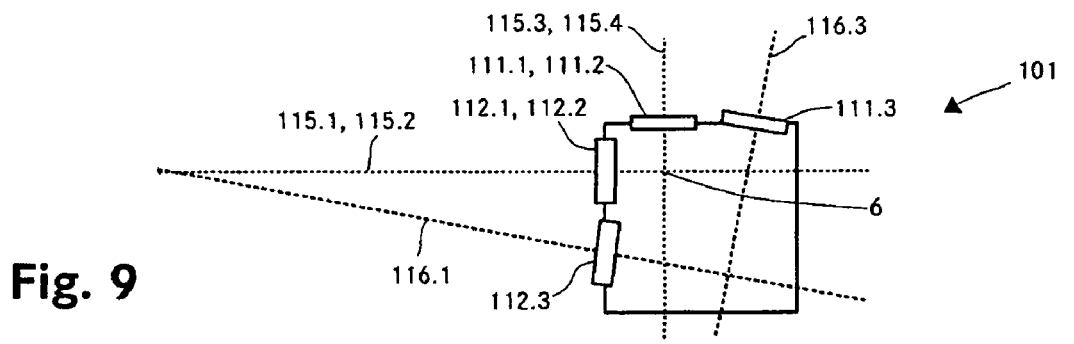
FIG. 9 shows a diagrammatic illustration of the side view of a lens barrel for a Greenough stereomicroscope in a first position.
Figure 10:
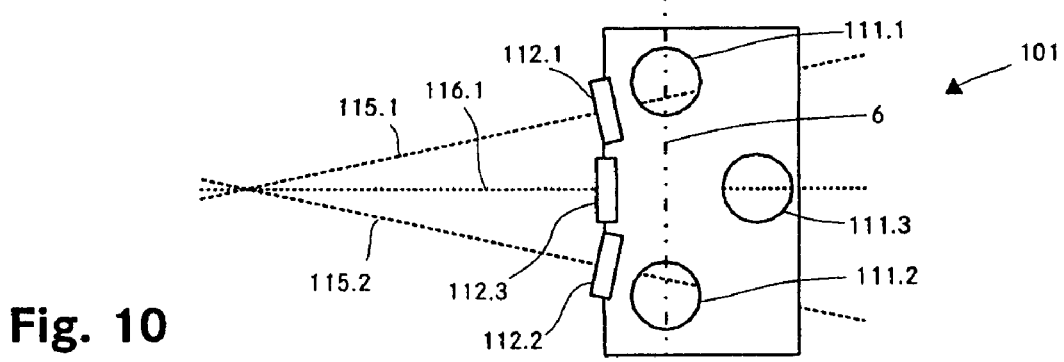
FIG. 10 shows a diagrammatic illustration of the lens barrel from FIG. 9 in a view from above.

FIG. 9 shows the lens barrel 101 diagrammatically in a side view of a first position in which the beam paths 115.1, 115.2, 116.1 are switched to be active, that is to say switched into the beam path of the associated optical component. FIG. 10 shows the lens barrel 101 in this first position, in a diagrammatic view from above.

Figure 11:
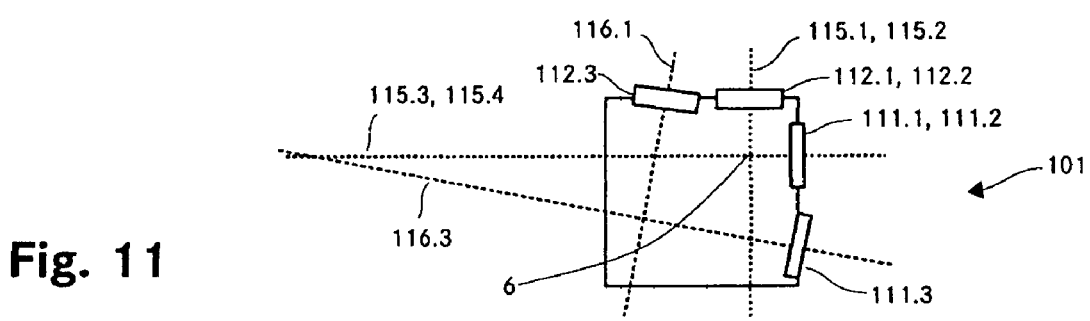
FIG. 11 shows a diagrammatic illustration of the lens barrel from FIG. 9 in a second position.
Figure 12:
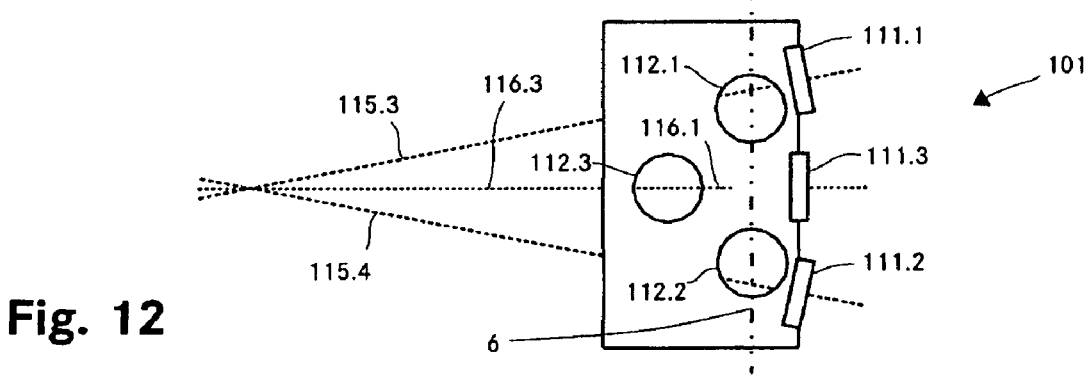
FIG. 12 shows a diagrammatic illustration of the lens barrel from FIG. 11 in a view from above.

FIG. 11 shows the lens barrel 101 diagrammatically in a side view of a second position, in which the beam paths 115.3, 115.4, 116.3 are switched to be active, that is to say are switched into the beam path of the associated optical component, and FIG. 12 shows the lens barrel 101 in this second position, in a diagrammatic view from above.

Also respectively illustrated is the rotation axis 6 (as a point in FIGS. 9 and 11, and as a line in FIGS. 10 and 12), about which the lens barrel 101 can be rotated from the first into the second position, and vice versa. In the example illustrated, the lens barrel 101 is rotated by 90 degrees in the clockwise sense from the first position, shown in FIGS. 9 and 10, into the second position, shown in FIGS. 11 and 12.

Although the lens barrel has been described in conjunction with the drawings chiefly as a magnification changer, the changing optics can also be designed in such a way that, instead of it being possible to achieve various imaging magnifications, it is possible to vary other imaging properties, depending on the position of the changing optics. Thus, for example, the illumination spectrum for illuminating the object to be imaged can be varied by virtue of the fact that, for example, the imaging optics used in the changing optics pass through or filter out different spectral regions. However, it is also possible to vary the illumination level or the size of the illuminated region of the object to be imaged. For example, the illumination can comprise areal illumination of the eye, or else can with a pattern, expedient for the respective application, such as, for example, with small circular areas, with a strip pattern or else with a single gap be performed, it being possible for such a pattern to be invariable, or else variable in time and/or space. Of course, it is also possible to provide different measurement or treatment beams, for example by means of coherent radiation of high energy density (laser radiation), for example for scanning and/or treating specific area in or on the eye. The changing optics can, however, also be designed for varying other imaging properties. Depending on the position, it is, for example, possible to vary the size of the image produced, or else to vary the brightness of the image. It is also possible to design the changing optics in such a way that different wavelengths are absorbed depending on their position. In order to achieve these different imaging and/or illumination properties, the imaging optics (previously chiefly denoted as lenses or lens arrangements for changing the imaging magnification) inserted into the respective beam paths of the changing optics can be replaced by imaging optics with the desired properties.

Of course, it is also possible to design the changing optics in such a way that two or more of these properties can be changed in combination.

It may be stated in summary that the invention provides a compact, cost effective optical component which is easy to produce and with the aid of which it is possible to provide two beam paths for a stereoscopic image of an object and one or more additional beam paths for an additional monoscopic or stereoscopic image(s) for observing or further processing or for illuminating the object. Here, the full luminous level is respectively available for each of these images, that is to say there is no need for beam splitters which split into two individual beam paths the light which runs along one beam path. The various beam paths are guided separately starting from the beginning, thus resulting in imaging or illumination which is of high quality and of high light gathering power. In addition, a plurality of different imaging and illuminating properties can respectively be selected for each of these images by switching over the optical component, for example by rotating the associated changing optics from one position into another position. Setting or selecting one of the possible images can be performed separately for each of the beam paths, as well, but can also preferably be performed simultaneously by actuating a common setting mechanism for all the beam paths.

The invention claimed is:

1. Optical component, comprising:
a pair of beam paths;
a changing optics comprising two pairs of beam paths, the changing optics being movably fastened in the optical component in such a way that the two beam paths of one of the pairs of beam paths of the changing optics can optionally be inserted in a beam section of the two beam paths of the optical component; and
at least one additional beam path assigned to the two beam paths,
the changing optics comprises per pair of beam paths at least one additional beam path assigned to the respective pair and spatially separated therefrom,
the changing optics is arranged such that, during the optional insertion of the two beam paths of one of the pairs of beam paths of the changing optics in the two beam paths of the optical component, the additional beam path of the changing optics which is assigned to this pair can simultaneously be inserted into a beam section of the additional beam path of the optical component,
the changing optics comprises an imaging optics for at least one of the pairs of beam paths and at least one of the pairs of additional beam paths,
the changing optics comprises a carrier device which can be rotated about a rotation axis and on which all the imaging optics are fastened and which comprises setting means with the aid of which the changing optics can be rotated about the rotation axis.

2. Optical component according to claim 1, further comprising exactly two additional beam paths assigned to the two beam paths, and the changing optics likewise comprises per pair of beam paths exactly two additional beam paths assigned to the respective pair of beam paths, the two beam paths of each pair of beam paths of the changing optics defining a first plane, and the two additional beam paths assigned to this pair respectively defining a second plane, the two planes respectively being mutually perpendicular, and a line of intersection of the two planes respectively lying between the two beam paths of the relevant pair.

3. Optical component according to claim 1, wherein the imaging optics is a lens arrangement.

4. Optical component according to claim 1, wherein the setting means can be rotated about the rotation axis manually.

5. Optical component according to claim 1, further comprising a housing, wherein the housing comprises an aperture, arranged on the object side, for the beam paths of the optical component and for the additional beam paths of the optical component, at least one first aperture, arranged on the observer side, for the beam paths of the optical component, and at least one second aperture, arranged on the observer side and in a fashion spatially separated from the first exit aperture, for the additional beam paths.

6. Optical component according to claim 5, further comprising a deflecting device, wherein the deflecting device comprises a mirror, for deflecting the additional beam paths to the second aperture.

7. Optical component according to claim 1, in which the two beam paths of the optical component run parallel in the beam section into which the two beam paths can be inserted, and the two beam paths of one pair of beam paths of the changing optics also run parallel to one another and parallel to the additional beam path assigned to this pair.

8. Optical component according to claim 7, in which the changing optics for at least one of the pairs of beam paths comprises a lens arrangement designed for optically imaging from infinity to infinity and for direct imaging and having a positive lens and a diverging lens.

9. Optical component according to claim 1 for an optical examination device having two beam paths for stereoscopic imaging of an object to be imaged, it being possible to connect the optical component optionally to the examination device in such a way that the beam paths of the optical component coincide with a section of the beam paths of the examination device.

10. Optical examination device having two beam paths for stereoscopically observing an object to be imaged, wherein the examination device comprises an optical component according to claim 1, the optical component being connected to the examination device in such a way that the beam paths of the optical component form a section of the beam paths of the examination device.

11. Optical examination device according to claim 10, further comprising an objective lens and two eyepieces, and the optical component is inserted into the beam paths of the optical examination device between the objective lens and the eyepieces.

12. Optical examination device according to claim 10, further comprising an optical imaging device, and the at least one additional beam path of the optical component can be deflected to the imaging device with the aid of a deflecting device.

13. Optical examination device according to claim 12, further comprising illuminating means for illuminating the object to be imaged by means of the at least one additional beam path.

* * * * *